United States Patent
Togawa et al.

(10) Patent No.: US 7,242,473 B2
(45) Date of Patent: Jul. 10, 2007

(54) PARTICLE SIZE DISTRIBUTION ANALYZER

(75) Inventors: Yoshiaki Togawa, Kyoto (JP); Hiroyuki Kitamura, Kyoto (JP); Takeshi Shimizu, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 11/510,360

(22) Filed: Aug. 25, 2006

(65) Prior Publication Data
US 2007/0046937 A1    Mar. 1, 2007

(30) Foreign Application Priority Data
Aug. 29, 2005    (JP) ............................ P2005-248257

(51) Int. Cl.
*G01N 15/02* (2006.01)
(52) U.S. Cl. ...................................... 356/335
(58) Field of Classification Search ................ None
See application file for complete search history.

(56) References Cited

U.S. PATENT DOCUMENTS 5,532,942 A * 7/1996 Kitamura et al. ........... 700/269

| | | | |
|---|---|---|---|
| 6,610,343 B2 * | 8/2003 | Purtle et al. | 426/430 |
| 6,741,350 B2 * | 5/2004 | Ikeda et al. | 356/336 |
| 2003/0147074 A1 | 8/2003 | Yamaguchi et al. | |

FOREIGN PATENT DOCUMENTS

| JP | 2001-0741639 | 3/2001 |
|---|---|---|
| JP | 2003-185558 | 3/2003 |

* cited by examiner

Primary Examiner—Tu T. Nguyen (57) ABSTRACT

An data processing system 4 includes: an integral part 43 which integrates, by two mutually different times, light intensities indicating light intensity signals outputted from light detectors 24 respectively provided for detecting intensities of scattered light and transmitted light generated by irradiating a sample powder S with light and then outputs each of the integrated values; an actuator control part 44 which generates and outputs a control signal for a vibration actuator 32 which drops the sample powder S stored in a sample housing so that one of the integrated values of light intensity outputted from the integral part 43 becomes closer to a set value previously defined; and a particle size distribution calculation part 45 which calculates the particle size distribution of the sample powder S based on another of the integrated values of light intensity outputted from the integral part 43.

2 Claims, 6 Drawing Sheets

PARTICLE SIZE DISTRIBUTION ANALYZER

BACKGROUND OF THE INVENTION

1. Field of the Invention

The present invention relates to a dry-type particle size distribution analyzer which drops a sample powder at a predetermined flow rate from a sample housing by vibrating the sample housing, supplies the dropped sample powder to a flow cell, and irradiates the sample powder with light to measure the particle size distribution.

2. Description of the Background Art

In the dry-type particle size distribution analyzer of this kind, for example, as shown in Japanese Unexamined Patent Publication No. 2003-185558, with a sample housing supported by a plate spring, absorption by an electrical magnet against the plate spring is performed without a break to thereby vibrate the sample housing whereby the sample powder is dropped and supplied to the flow cell.

In such a dry-type particle size distribution analyzer, an appropriate sample supply rate needs to be set for the measurement. The sample supply rate is reflected on the intensity of transmitted light (transmittance) and the intensity of scattered light; thus, conventionally, in order to define the sample supply rate, the operator monitors the intensity of transmitted light (transmittance) and the intensity of scattered light and adjusts the amplitude, cycle, waveform, and the like of vibration so that the values thereof reach their respective desired values.

However, these monitoring and adjustment is required not only at the initial stage but also during the measurement as needed, which involves time-consuming operation, for reasons such as that, even with same vibration, the sample supply state gradually changes depending on the amount of the sample powder remaining in the sample housing.

Further, this adjustment operation depends on the skill level of the operator. Thus, the measurement results may differ among different operators, and the adjustment operation may require some time thus leading to waste of the sample.

SUMMARY OF THE INVENTION

Thus, to solve the problem described above, the present invention has been made, and it is a major object of the present invention to provide a particle size distribution analyzer which is capable of reducing the load imposed on the operator and also capable of improving measurement accuracy and measurement reproducibility, and further which prevents waste of the sample powder.

More specifically, according to one aspect of the present invention, a particle size distribution analyzer includes: a sample housing which stores the sample powder; a vibration actuator which vibrates the sample housing to thereby drop the sample powder through a sample drop hole formed in the sample housing; a light source which irradiates the dropping sample powder with light; a light detector which detects intensity of scattered light and/or transmitted light generated by the irradiation of the sample powder with the light and then outputs the intensity as a light intensity signal; and an data processing system which, based on the light intensity, controls the vibration actuator and also calculates the particle size distribution of the sample powder. The data processing system includes: an integral part which integrates the light intensity indicating the light intensity signal by two mutually different times and outputs each of the integrated values; an actuator control part which generates and outputs a control signal for the vibration actuator so that one of the integrated values of light intensity outputted from the integral part becomes closer to a set value previously defined; and a particle size distribution calculation part which calculates the particle size distribution of the sample powder based on another of the integrated values of light intensity outputted from the integral part. Here, "scattered light" may include diffracted light and "light intensity" corresponds to the intensity of transmitted light, or transmittance, or intensity data obtained from the intensity of transmitted light.

Control of the vibration of the sample housing usually requires faster response than the particle size distribution calculation; thus, it is preferable that integral time of light intensity used for the vibration actuator be set shorter than integral time of light intensity used for the particle size distribution calculation.

According to the present invention configured in this manner, the operator is first only required to set a target integrated value of light intensity, for example, target transmittance or a target intensity of transmitted light, or a target intensity of scattered light, and thus not required to make adjustment while monitoring a supply amount of the sample powder, thus largely reducing the load of operation.

Moreover, the supply amount of the sample powder is automatically adjusted, which does not involves time-consuming operation, thereby permitting suppressing waste of the sample powder and thus practically permitting reduction in the amount of the sample powder required for measurement.

Moreover, a suitable amount of the sample powder can be reliably supplied for the measurement, thus improving the measurement accuracy. Furthermore, the sample supply amount can be kept constant, thus improving the measurement reproducibility. In addition, even a different operator can maintain the uniform sample supply amount, thus providing the same measurement results.

Further, existing light detectors for measurement of particle size distribution are also used for operation of automatic control of the sample supply amount, thus permitting the automatic control of the supply amount to be achieved just by providing a simple improvement in the existing devices.

DETAILED DESCRIPTION OF THE PREFERRED EMBODIMENTS

Hereinafter, one embodiment of the present invention will be described referring to the accompanying drawings. A dry-type particle size distribution analyzer 1 according to the present embodiment is mainly provided with, as shown in the overall outline of FIG. 1, a measuring mechanism 2, a sample feed mechanism 3, and an data processing system 4.

Figure 1:
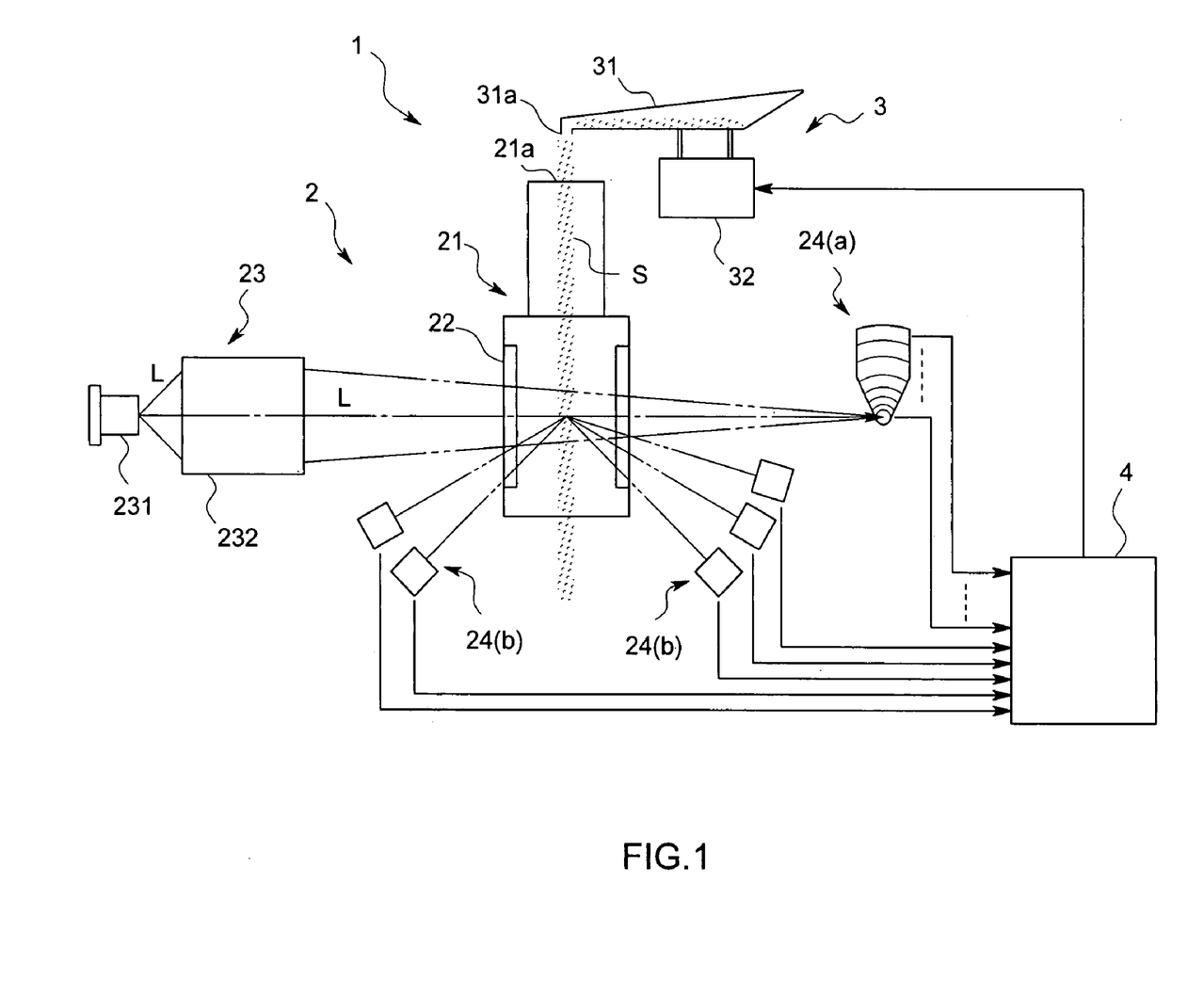
FIG. 1 is an overall schematic diagram of a particle size distribution analyzer according to one embodiment of the present invention.

First, the measuring mechanism 2 will be described. This measuring mechanism 2 is provided with: a sample flow path 21 having, for example, in the middle thereof a transparent flow cell 22 of a cylindrical shape which extends vertically; a light source 23 which irradiates a sample powder S dropping inside the flow cell 22 with laser light L; and a plurality of light detectors 24 which are arranged around the flow cell 22 and which receive scattered light and/or diffracted light and transmitted light generated upon the irradiation of the sample powder S with the laser light L.

The light source 23 is provided with: a semiconductor laser 231; and a condensing lens 232 arranged in front thereof, and is designed so that the emitted laser light L is converged on one of the light detectors 24, to be described later, which is located on the optical axis and which is provided as a light detector for transmitted light detection.

The sample flow path 21 has a sample feed port 21a opening upward for introducing the sample powder S inside, and has downstream thereof an ejector part, a compressed air feed path, a straightening plate, and the like, all not shown, further downstream of which the flow cell 22 is formed. Downstream of the flow cell 22, an absorption device, not shown, is provided, which collects the sample powder S which has passed through the flow cell 22.

The light detectors 24 are classified into: a first light detector group 24(a) which is arranged substantially opposite to the laser 23 with the flow cell 22 in between for the purpose of detecting narrow-angle scattered light scattering forward and the transmitted light; and a second light detector group 24(b) which is arranged around the flow cell 22 in a scattered for the purpose of detecting wide-angle scattered light scattering rearward or to the side. Each of these light detectors 24 outputs, to the data processing system 4 to be described later, a light intensity signal having a value in accordance with the intensity of light received.

Figure 2:
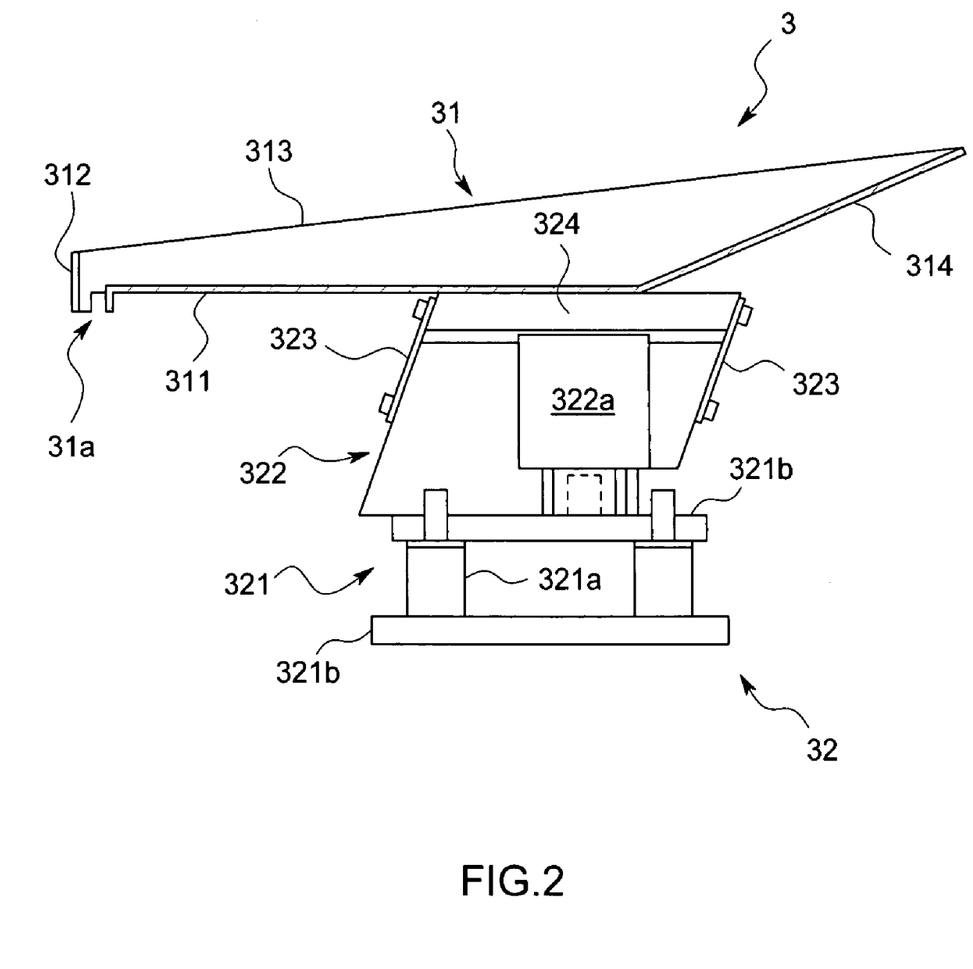
FIG. 2 is a general side view showing a sample feed mechanism (feeder) of the particle size distribution analyzer in the same embodiment.
Figure 3:
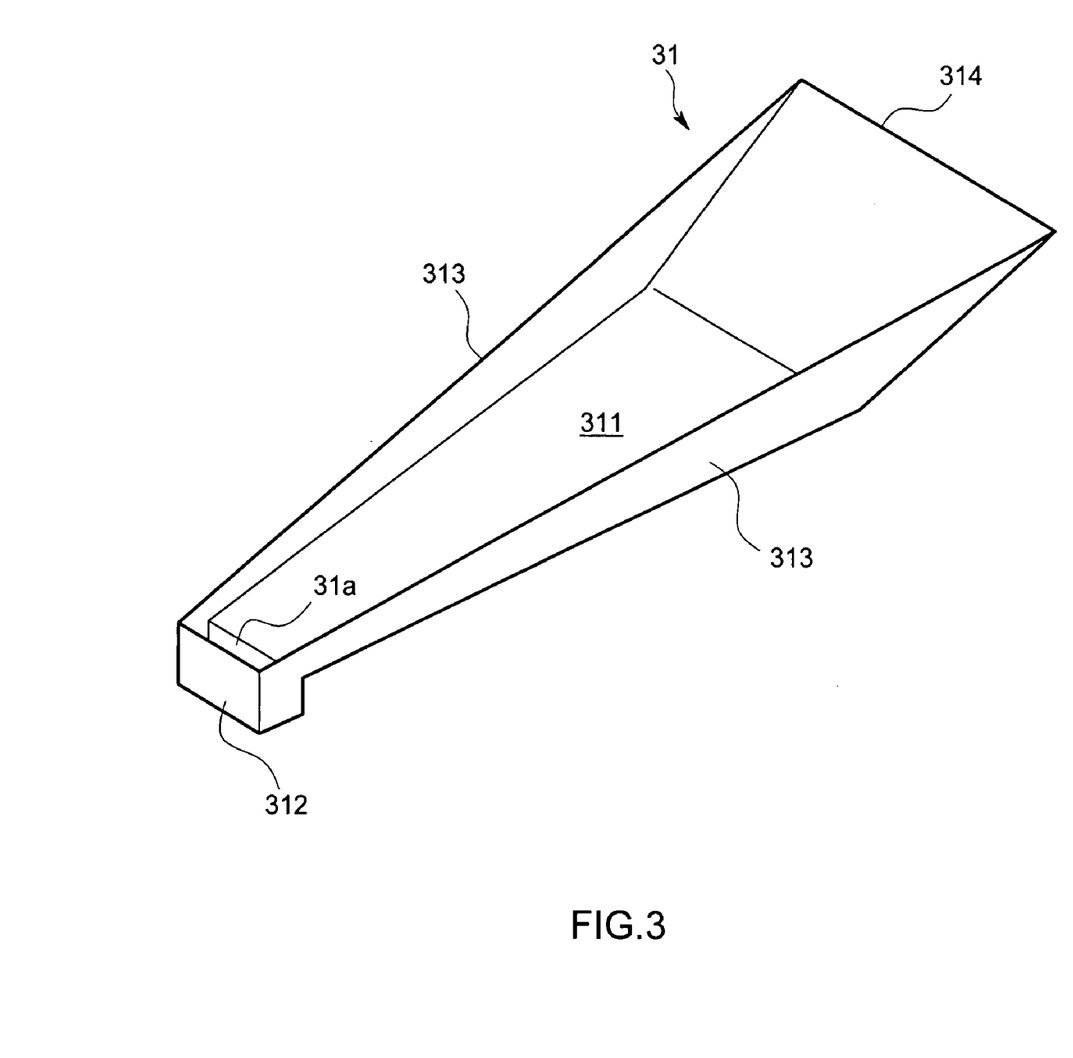
FIG. 3 is a perspective view showing a shoot of the particle size distribution analyzer in the same embodiment.

Next, the sample feed mechanism 3 will be described. This sample feed mechanism 3 (hereinafter, also referred to as a feeder) is so formed as to be provided with: as shown in FIG. 2, a shoot 31 as a sample housing for storing the sample powder S; a vibration actuator 32 which supports and also vibrates this shoot 31. The shoot 31, as shown in FIGS. 2 and 3, is formed in the shape of a flat-box opening upward, and is composed of a bottom plate 311 formed in an isosceles trapezoidal shape as viewed in plane and rising plates 312, 313, and 314 rising from the periphery of the bottom plate 311. Of these rising plates 312, 313, and 314, the rising plate 312 located at the short-edge side (hereinafter, referred to as front end side) of the bottom plate 311 and the rising plate 313 located at the side-edge side thereof rise perpendicularly while the rising plate 314 located at the long-edge side (hereinafter, referred to as rear-end side) of the bottom plate 311 tilts obliquely. Through the front end part of the bottom plate 311; a sample drop hole 31a is punctured which is formed in a rectangular shape.

The vibration actuator 32 is provided with: as shown in FIG. 2, a base 321 so formed as to have base plates 321b respectively provided at the top and bottom of an anti-vibration member 321a of rubber or the like; an electrical magnet unit 322 fitted on this base 321; a pair of plate springs 323 rising mutually parallelly and obliquely from the front and rear end parts of the electrical magnet unit 322; and a vibration plate 324 supported on the top end parts of the plate springs 323. The shoot 31 is arranged with the bottom plate 311 thereof loaded and fixed on the top surface of the vibration plate 324 so that the sample drop hole 31a is located right above the sample feed port 21a. The vibration plate 324 is formed of raw material, such as iron or the like, which is absorbed by a magnetic force, and is so configured as to be located above an electrical magnet 322a slightly separately therefrom during normal operation when no power is distributed to the electrical magnet 322a so that the bottom plate 311 of the shoot 31 is oriented horizontally.

Figure 4:
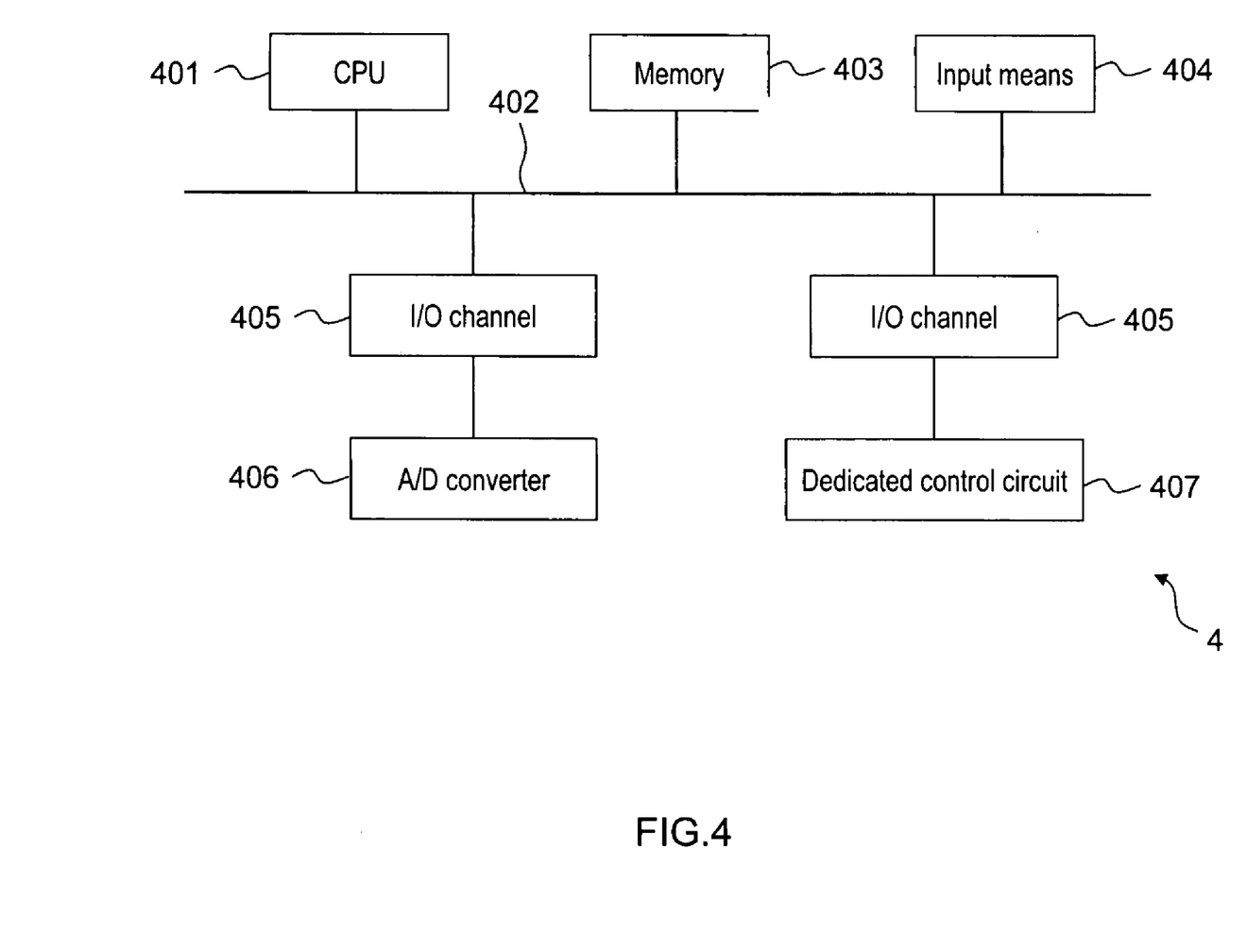
FIG. 4 is a schematic system block diagram showing an data processing system of the particle size distribution analyzer in the same embodiment.

The data processing system 4, as in a conceptual diagram of FIG. 4 showing the system thereof, is provided with: a so-called computer composed of a CPU 401, a bus 402, a memory 403, input means 404, and the like; and peripheral devices such as an A/D converter 406, a buffer (not shown), a dedicated control circuit 407 and the like which are connected to the computer via an I/O channel 405. This data processing system 4 may be physically integrated together, or may be provided in a manner such that dedicated electrical circuits and the like are connected to a general-purpose computer, that is, may be arranged such that a plurality of devices are arranged in a scattered manner while being connected together through communication.

Figure 5:
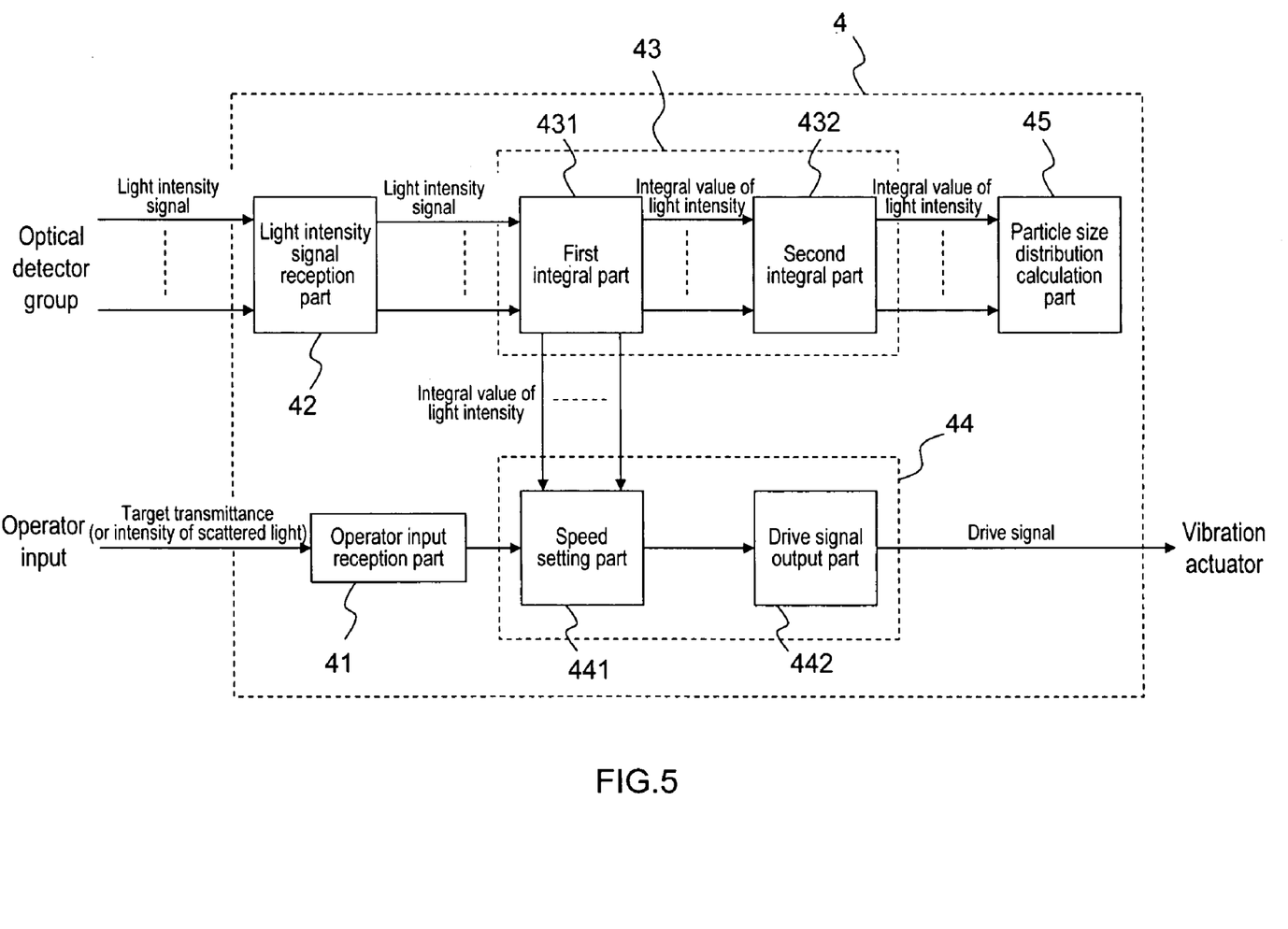
FIG. 5 is a functional block diagram of the data processing system in the same embodiment.

This data processing system 4, as a result of cooperative operation between the CPU 401 and the peripheral devices or independent operation of the internal circuits in accordance with a program stored in the memory 403, fulfills a function as an operator input reception part 41, a light intensity signal reception part 42, an integral part 43, an actuator control part 44, and a particle size distribution calculation part 45 and the like, as shown in FIG. 5.

Hereinafter, each of the parts will be described.

The operator input reception part 41 receives a configuration parameter inputted by the operator by using the input means 404 such as a keyboard, a mouse, or the like, and outputs it to the actuator control part 44 to be described later. The configuration parameter corresponds to the target transmittance (or intensity of transmitted light) or the target intensity of scattered light.

The light intensity signal reception part 42 receives light intensity signals from the light detectors 24 by way of amplification, A/D conversion, or the like, and outputs them to the integral part 43 to be described later. This light intensity signal reception part 42 is mainly composed of the buffer, an amplifier, the A/D converter 406, and the like.

The integral part 43 is composed of a first integral part 431 and a second integral part 432 which are serially provided and each of which is formed of dedicated hardware. Note that these parts may be of course built with software. The first integral part 431 integrates by given period of time the value of a light intensity signal outputted from the light intensity signal reception part 42, and outputs it to the actuator control part 44 and the second integral part 432. The second integral part 432 further integrates by a given period of time the value outputted from the first the integral part 431, that is, a first integrated value of light intensity, and then outputs it to the particle size distribution calculation part 45.

The actuator control part 44 performs feedback control on the feeder 3 so that the first integrated value of light intensity outputted from the first integral part 431 becomes closer to the target transmittance (or intensity of scattered light) received by the operator input reception part 41. The actuator control part 44 is provided with: a speed setting part 441 which calculates a difference between the first integrated value of light intensity and the target transmittance (or intensity of scattered light) and then sets the feeder speed in accordance with this difference; and a drive signal output part 442 which generates a drive signal for causing vibration corresponding to the feeder speed and then outputs it to the vibration actuator 32. If the value received by the operator input reception part 41 is the transmittance, the speed setting part 441 sets the feeder speed by using the value from the light detector 24 provided for transmitted light detection; if the values is the intensity of scattered light, the speed setting part 441 sets the feeder speed by using the value from the light detector 24 provided for scattered light detection. The drive signal output part 442 is formed of dedicated hardware in the embodiment. The drive signal is, for example, an ON/OFF pulse signal, whose cycle, amplitude, and ON/OFF ratio define the drop flow rate of the sample powder S.

Next, the operation of this dry-type particle size distribution analyzer 1 will be described below.

First, as a configuration parameter for the sample supply amount, the operator sets not "the speed of the feeder" but the transmittance (intensity of transmitted light) or the intensity of scattered light by using the input means 404 (keyboard, mouse, or the like). This target set value is received by the operator input reception part 41.

Meanwhile, the light intensity signal reception part 42 receives light intensity signals from the light detectors 24 and outputs them to the first integral part 431.

Next, the first integral part 431 integrates by a given period of time the values of the light intensity signals from the light intensity signal reception part 42, and transmits them to the actuator control part 44 and the second integral part 432.

In the actuator control part 44, the speed setting part 441 calculates a difference between the first integrated value of light intensity integrated by the first integral part 431 and the transmittance (or intensity of scattered light) set by the operator, and sets the feeder speed in accordance with this difference. Then, the drive signal output part 442 generates a drive signal for causing vibration corresponding to this feeder speed, and outputs it to the vibration actuator 32.

As a result, the electrical magnet 322a in the vibration actuator 32 is repeatedly turned on and off in a manner defined by the drive signal, so that, under the interaction between the absorption force by this electrical magnet 322a and the separation force by the plate spring, the vibration plate 324 and the shoot 31 fixed thereon vibrate. Then, the sample powder S inside the shoot 31 is shaken and gradually flows into the flow cell 22 through the sample drop hole 31a.

On the other hand, the second integral part 432 further integrates the value of light intensity signal integrated by the first integral part 431 by a time suitable for particle size calculation, and outputs it to the particle size distribution calculation part 45. Then, the particle size distribution calculation part 45, based on the value outputted from the second integral part 432 (second integrated value of light intensity), calculates the particle size distribution of the sample powder S. The calculation of the particle size distribution is performed in the same manner as a conventional method, and thus is omitted from description.

With the particle size distribution analyzer 1 configured in this manner according to the present embodiment, the operator is first only required to set the transmittance (or intensity of scattered light), and thus not required to make adjustment while monitoring the supply amount of the sample powder S, thus largely reducing the load of operation. Moreover, the supply amount of the sample powder S is automatically adjusted, which does not involves time-consuming operation, thereby permitting suppressing waste of the sample powder S and thus practically permitting reduction in the amount of the sample powder S required for the measurement.

Moreover, the light detectors 24 for measurement of the particle size distribution are also used for the operation of this automatic control of the supply amount, which requires no new special detector, thus permitting the automatic control of the supply amount to be achieved just by providing a simple improvement in the existing devices.

Further, the suitable amount of the sample powder can be reliably supplied for the measurement, thus improving the measurement accuracy. Furthermore, the sample supply amount can be kept constant, thus improving the measurement reproducibility. In addition, even a different operator can maintain the uniform sample supply amount, thus providing the same measurement results.

Note that the present invention is not limited to the present embodiment.

Examples of methods of setting a target set value of the sample supply amount by the operator include:
previously inputting the target set value before the measurement;
changing and inputting the target set value during the feedback control; and
retrieving a numerical value which is added to "measurement data file" or "measurement condition file" recorded on a memory or a disc.

Examples of methods of setting the rate of supply by the feeder at start of the control include:
using the speed which was optimized and stored in the past measurement;
using a numerical value set by the operator before the measurement; and
retrieving a numerical value which is added to "measurement data file" or "measurement condition file" recorded on the memory or the disc.

Examples of the sample feeder include those which:
vibrates the shoot 31 by the absorption force of a solenoid being provided as a drive source;
vibrates the shoot 31 by a rotary force of a motor being provided as a drive source;
vibrates a screen by the rotary force of the motor being provided as the drive source; and
drives a belt, a roller, the disc, and a rail loading the sample powder S thereon by the motor.

Figure 6:
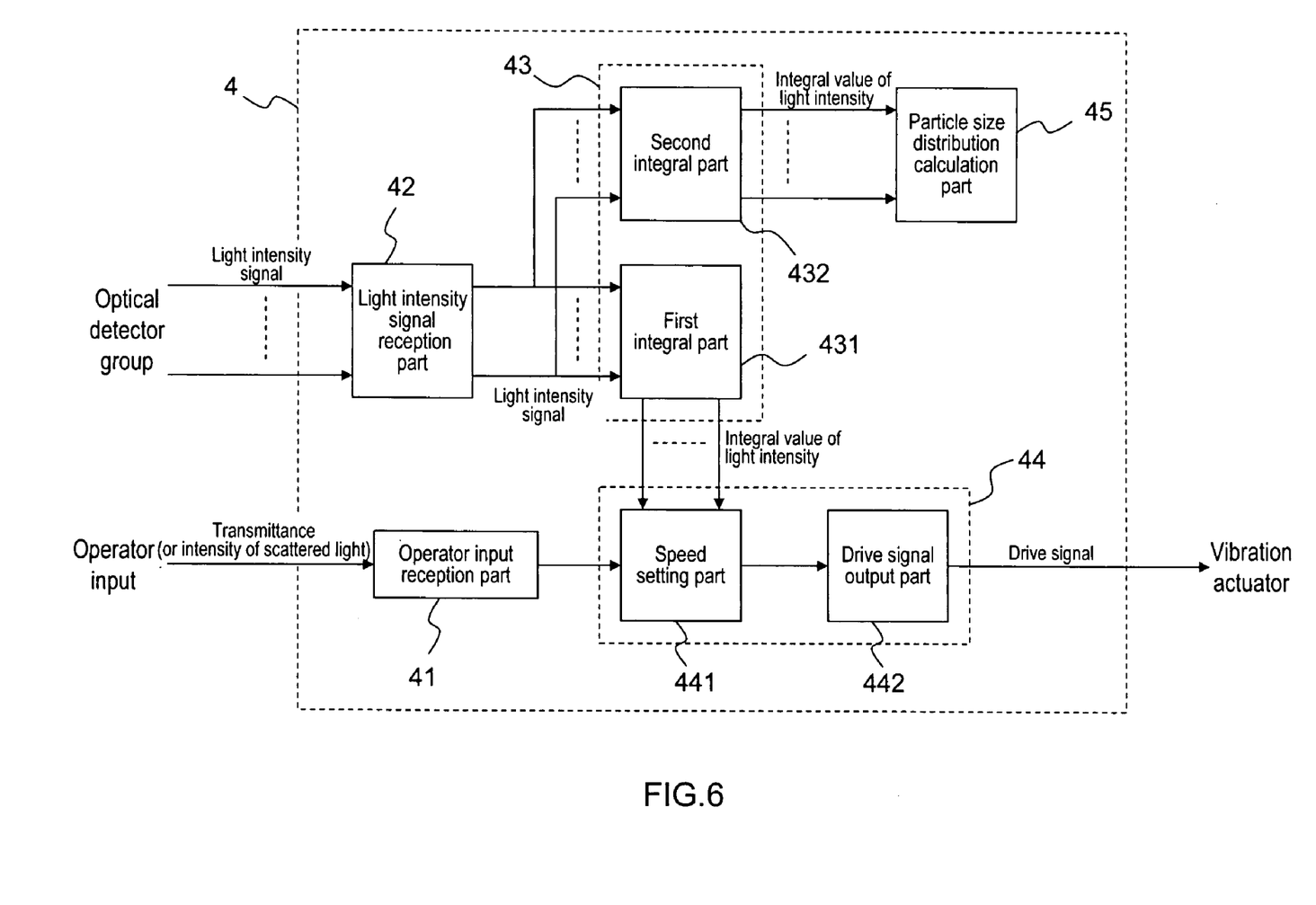
FIG. 6 is a functional block diagram of an data processing system in another embodiment of the present invention.

The first and second integral parts 431 and 432 having different integration times may be provided in parallel as shown in FIG. 6. In this figure, those corresponding to the above-mentioned embodiment are provided with the same numerals.

The present invention permits various modifications without departing from the scope and sprit of the present invention.

What is claimed is:

1. A particle size distribution analyzer comprising: a sample housing which stores a sample powder; a vibration actuator which vibrates the sample housing to thereby drop the sample powder from the sample housing; a light source which irradiates the dropping sample powder with light; a light detector which detects intensity of scattered light and/or transmitted light generated by the irradiation of the sample powder with the light and then outputs the intensity as a light intensity signal; and a data processing system which, based on the light intensity, controls the vibration actuator and also calculates particle size distribution of the sample powder, wherein the data processing system comprises: an integral part which integrates the light intensity indicating the light intensity signal by two mutually different times and outputs each of the integrated values; an actuator control part which generates and outputs a control signal for the vibration actuator so that one of the integrated values of light intensity outputted from the integral part becomes closer to a set value previously defined; and a particle size distribution calculation part which calculates the particle size distribution of the sample powder based on another of the integrated values of light intensity outputted from the integral part.

2. The particle size distribution analyzer according to claim 1, wherein the integral time of light intensity used for the vibration actuator is shorter than the integral time of light intensity used for the particle size distribution calculation.

* * * * *